United States Patent [19]

Dawson et al.

[11] Patent Number: 4,490,414
[45] Date of Patent: Dec. 25, 1984

[54] OPEN CHAIN ANALOGUES OF RETINOIC ACID

[75] Inventors: Marcia I. Dawson, Los Altos; Rebecca L. S. Chan, Palo Alto, both of Calif.

[73] Assignee: SRI International, Menlo Park, Calif.

[21] Appl. No.: 493,507

[22] Filed: May 11, 1983

[51] Int. Cl.³ .................. C07C 57/03; C07C 69/587; C07C 103/133; A61K 31/23
[52] U.S. Cl. ................ 424/312; 260/410.5; 260/410.6; 260/410.9; 260/413; 260/404; 424/314; 424/318; 424/320; 424/324; 260/410.9 V
[58] Field of Search .......... 260/410.5, 410.6, 410.9 V, 260/410.9 M, 413 L, 404; 424/312, 314, 318, 320, 324

[56] References Cited

U.S. PATENT DOCUMENTS

| | | | |
|---|---|---|---|
| 3,746,730 | 7/1973 | Marbet | 260/413 L |
| 3,781,314 | 12/1973 | Bollag et al. | 260/410.9 M |
| 4,107,193 | 8/1978 | Kijima et al. | 260/413 L X |
| 4,147,708 | 4/1979 | Manchand | 260/413 L |

*Primary Examiner*—Thomas A. Waltz

*Attorney, Agent, or Firm*—Ciotti & Murashige

[57] ABSTRACT

Open ring retinoic acid analogues and 2Z isomers of the formula

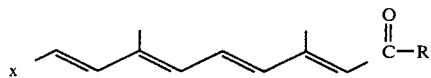

where X is

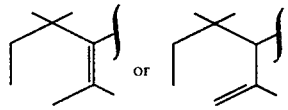

and R is hydroxy, alkoxy with 0 or 1 hydroxy substituent, aroxy with 0 or 1 hydroxy or alkoxy-monosubstituted phenoxy or $NR^1R^2$ where $R^1$ is hydrogen, alkyl, or aryl and $R^2$ is alkyl or aryl are disclosed. These retinoids are useful as chemopreventive agents for inhibiting tumor promotion in epithelial cells and for treating nonmalignant skin disorders.

12 Claims, No Drawings

OPEN CHAIN ANALOGUES OF RETINOIC ACID

REFERENCE TO GOVERNMENT GRANT

The invention described herein was made in the course of work under a grant from the National Cancer Institute.

DESCRIPTION

1. Technical Field

The invention is in the fields of retinoid chemistry and chemotherapy and relates to retinoic acid analogues. More particularly, the invention relates to certain retinoic acid analogues with open ring modifications.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, R. K., et al, *Advances in Enzyme Regulation* V.17, Ed. Weber, G., Pergamon Press (1979); Verma, A. K., et al, *Cancer Res* (1979) 39:419–427; Dawson, M. I., et al, *J Med Chem* (1980) 23:1013–1022, *J Med Chem* (1981) 24:583–592 and *J Med Chem* (1981) 24:1214–1223.

The latter Dawson, M. I., et al, articles report the preparation of several retinoic acid analogues with ring modifications and their stereoisomers. Some of these retinoids exhibited biological activity in the ornithine decarboxylase (ODC) assay which assay is described by Verma, A. K. and Boutwell, R. K., *Cancer Res* (1977) 37:2196–2201. However, none of these compounds were acyclic.

A principal object of this invention is to provide open chain retinoic acid analogues in which the b-cyclogeranylidene ring is open at the 3 and 4 positions and which are biologically active and may exhibit less toxicity than retinoic acid and other retinoids.

DISCLOSURE OF THE INVENTION

The open chain retinoic acid analogues of the invention are the 2E,4E,6E,8E compounds of the formula:

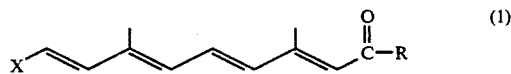

and corresponding 2Z isomers
where X is

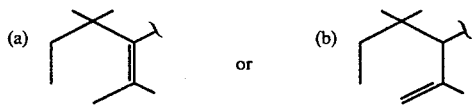

and R is hydroxy, alkoxy with 0 or 1 hydroxy substituent, aroxy, or $NR^1R^2$ where $R^1$ is hydrogen, alkyl with 0 or 1 hydroxy substituent, or aryl, and $R^2$ is alkyl with 0 or 1 hydroxy substituent or aryl.

When used as pharmaceuticals, eg, for the treatment, prevention, and reversal of precancerous epithelial cell transformations, epithelial cancer, psoriasis, acne, keratosis and other skin diseases, one or more of these retinoids is combined with a suitable pharmaceutically acceptable carrier and an effective dose thereof is administered to the patient.

MODES FOR CARRYING OUT THE INVENTION

The alkoxy groups represented by R will usually contain 1 to about 10 carbon atoms and have 0 or 1 hydroxy substituent, preferably 1 to 4 carbon atoms with 0 or 1 hydroxy substituent, and the aroxy groups represented thereby will usually be mononuclear and contain 6 to 15 carbon atoms and have 0 or 1 hydroxy substituent, more usually 6 to 10 carbon atoms with 0 or 1 hydroxy substituent. Preferred aroxy groups are phenoxy and hydroxy- or $C_1$-$C_4$ alkoxy-monosubstituted phenoxy. The alkoxy groups represented by R may be straight chain or branched chain. Examples of such alkoxy groups are methoxy, ethoxy, n-propoxy, i-propoxy, n-butoxy, s-butoxy, t-butoxy, n-pentoxy, n-hexoxy, 2-methylpentoxy, n-heptoxy, 2-hydroxyethoxy, 3-methylhexoxy, n-octoxy, and n-decoxy. Examples of aroxy groups are phenoxy, o-, m-, p-hydroxyphenoxy o-, m-, p-methoxyphenoxy, toloxy, cumoxy, xyloxy, and naphthoxy.

The alkyl groups represented by $R^1$ and $R^2$ may be straight chain or branched chain. They will typically each contain 1 to 8 carbon atoms with 0 or 1 hydroxy substituent, preferably 1 to 4 carbon atoms, and have 0 or 1 hydroxy substituent. Examples of such alkyl groups are methyl, ethyl, propyl, isopropyl, n-butyl, s-butyl, n-amyl, n-hexyl, 2-methylamyl, n-heptyl, 3-methylhexyl, n-octyl, hydroxymethyl, 2-hydroxyethyl, 3-hydroxypropyl, 2-hydroxyhexyl, and the like. The corresponding aryl groups represented by $R^1$ and $R^2$ may be substituted or unsubstituted mononuclear or polynuclear moieties. The substituents will usually be lower (ie, 1 to 4 carbon atoms) alkyl, monohydroxyalkyl, lower alkoxy, monohydroxyalkoxy, or hydroxy. When substituted, the group will usually be mono-substituted. Examples of such groups are phenyl, o-, m-, or p-hydroxyphenyl, o-, m-, or p-methoxyphenyl, ethylbenzyl, cumyl, and the like. These aryl groups will usually contain 6 to about 15 carbon atoms, more usually 6 to 10 carbon atoms. Phenyl, 4-hydroxyphenyl, and 4-methoxyphenyl are preferred aryl groups.

The acids (R=OH) represented by formula (1) are (E)-10-(1,1-dimethyl-1-propyl)-3,7,11-trimethyl-2,4,6,8,10-dodecapentaenoic acid and (E)-10-(1,1-dimethyl-1-propyl)-3,7,11-trimethyl-2,4,6,8,11 dodecapentaenoic acid.

Examples of esters (R=alkoxy, aroxy) represented by formula (1)(a) are:

Methyl (E)-10-(1,1-dimethyl-1-propyl)-3,7,11-trimethyl-2,4,6,8,10-dodecapentaenoate,
Ethyl (E)-10-(1,1-dimethyl-1-propyl)-3,7,11-trimethyl-2,4,6,8,10-dodecapentaenoate,
Isopropyl (E)-10-(1,1-dimethyl-1-propyl)-3,7,11-trimethyl-2,4,6,8,10-dodecapentaenoate,
Propyl (E)-10-(1,1-dimethyl-1-propyl)-3,7,11-trimethyl-2,4,6,8,10-dodecapentaenoate,
Butyl (E)-10-(1,1-dimethyl-1-propyl)-3,7,11-trimethyl-2,4,6,8,10-dodecapentaenoate,
Pentyl (E)-10-(1,1-dimethyl-1-propyl)-3,7,11-trimethyl-2,4,6,8,10-dodecapentaenoate,
Hexyl (E)-10-(1,1-dimethyl-1-propyl)-3,7,11-trimethyl-2,4,6,8,10-dodecapentaenoate,
Heptyl (E)-10-(1,1-dimethyl-1-propyl)-3,7,11-trimethyl-2,4,6,8,10-dodecapentaenoate, Octyl (E)-10-(1,1-dimethyl-1-propyl)-3,7,11-trimethyl-2,4,6,8,10-dodecapentaenoate,
Nonyl (E)-10-(1,1-dimethyl-1-propyl)-3,7,11-trimethyl-2,4,6,8,10-dodecapentaenoate,
Decyl (E)-10-(1,1-dimethyl-1-propyl)-3,7,11-trimethyl-2,4,6,8,10-dodecapentaenoate,
2-Hydroxyethyl (E)-10-(1,1-dimethyl-1-propyl)-3,7,11-trimethyl-2,4,6,8,10-dodecapentaenoate,
3-Hydroxypropyl (E)-10-(1,1-dimethyl-1-propyl)-3,7,11-trimethyl-2,4,6,8,10-dodecapentaenoate,
Phenyl (E)-10-(1,1-dimethyl-1-propyl)-3,7,11-trimethyl-2,4,6,8,10-dodecapentaenoate,
p-Hydroxyphenyl (E)-10-(1,1-dimethyl-1-propyl)-3,7,11-trimethyl-2,4,6,8,10-dodecapentaenoate,
o-Hydroxyphenyl (E)-10-(1,1-dimethyl-1-propyl)-3,7,11-trimethyl-2,4,6,8,10-dodecapentaenoate,
p-Methoxyphenyl (E)-10-(1,1-dimethyl-1-propyl)-3,7,11-trimethyl-2,4,6,8,10-dodecapentaenoate,
p-Isopropylphenyl (E)-10-(1,1-dimethyl-1-propyl)-3,7,11-trimethyl-2,4,6,8,10-dodecapentaenoate,
Tolyl (E)-10-(1,1-dimethyl-1-propyl)-3,7,11-trimethyl-2,4,6,8,10-dodecapentaenoate,
Naphthyl (E)-10-(1,1-dimethyl-1-propyl)-3,7,11-trimethyl-2,4,6,8,10-dodecapentaenoate, Examples of esters represented by formula (1)(b) are:
Methyl (E)-10-(1,1-dimethyl-1-propyl)-3,7,11-trimethyl-2,4,6,8,11-dodecapentaenoate,
Ethyl (E)-10-(1,1-dimethyl-1-propyl)-3,7,11-trimethyl-2,4,6,8,11-dodecapentaenoate,
Isopropyl (E)-10-(1,1-dimethyl-1-propyl)-3,7,11-trimethyl-2,4,6,8,11-dodecapentaenoate,
Propyl (E)-10-(1,1-dimethyl-1-propyl)-3,7,11-trimethyl-2,4,6,8,11-dodecapentaenoate,
Butyl (E)-10-(1,1-dimethyl-1-propyl)-3,7,11-trimethyl-2,4,6,8,11-dodecapentaenoate,
Pentyl (E)-10-(1,1-dimethyl-1-propyl)-3,7,11-trimethyl-2,4,6,8,11-dodecapentaenoate,
Hexyl (E)-10-(1,1-dimethyl-1-propyl)-3,7,11-trimethyl-2,4,6,8,11-dodecapentaenoate,
Heptyl (E)-10-(1,1-dimethyl-1-propyl)-3,7,11-trimethyl-2,4,6,8,11-dodecapentaenoate,
Octyl (E)-10-(1,1-dimethyl-1-propyl)-3,7,11-trimethyl-2,4,6,8,11-dodecapentaenoate,
Nonyl (E)-10-(1,1-dimethyl-1-propyl)-3,7,11-trimethyl-2,4,6,8,11-dodecapentaenoate,
Decyl (E)-10-(1,1-dimethyl-1-propyl)-3,7,11-trimethyl-2,4,6,8,11-dodecapentaenoate,
2-Hydroxyethyl (E)-10-(1,1-dimethyl-1-propyl)-3,7,11-trimethyl-2,4,6,8,11-dodecapentaenoate,
3-Hydroxypropyl (E)-10-(1,1-dimethyl-1-propyl)-3,7,11-trimethyl-2,4,6,8,11-dodecapentaenoate,
Phenyl (E)-10-(1,1-dimethyl-1-propyl)-3,7,11-trimethyl-2,4,6,8,11-dodecapentaenoate,
p-Hydroxyphenyl (E)-10-(1,1-dimethyl-1-propyl)-3,7,11-trimethyl-2,4,6,8,11-dodecapentaenoate,
o-Hydroxyphenyl (E)-10-(1,1-dimethyl-1-propyl)-3,7,11-trimethyl-2,4,6,8,11-dodecapentaenoate,
p-Methoxyphenyl (E)-10-(1,1-dimethyl-1-propyl)-3,7,11-trimethyl-2,4,6,8,11-dodecapentaenoate,
p-Isopropylphenyl (E)-10-(1,1-dimethyl-1-propyl)-3,7,11-trimethyl-2,4,6,8,11-dodecapentaenoate,
Tolyl (E)-10-(1,1-dimethyl-1-propyl)-3,7,11-trimethyl-2,4,6,8,11-dodecapentaenoate, and
Naphthyl (E)-10-(1,1-dimethyl-1-propyl)-3,7,11-trimethyl-2,4,6,8,11-dodecapentaenoate.

Examples of carboxamides (R=NR$^1$R$^2$) represented by formula (1)(a) are:
N-methyl (E)-10-(1,1-dimethyl-1-propyl)-3,7,11-trimethyl-2,4 6,8,10-dodecapentaenoamide,
N-isopropyl (E)-10-(1,1-dimethyl-1-propyl)-3,7,11-trimethyl-2,4,6,8,10-dodecapentaenoamide,
N-pentyl (E)-10-(1,1-dimethyl-1-propyl)-3,7,11-trimethyl-2,4,6,8,10-dodecapentaenoamide,
N-octyl (E)-10-(1,1-dimethyl-1-propyl)-3,7,11-trimethyl-2,4,6,8,10-dodecapentaenoamide,
N-2-hydroxyethyl (E)-10-(1,1-dimethyl-1-propyl)-3,7,11-trimethyl-2,4,6,8,10-dodecapentaenoamide,
N-3-hydroxypropyl (E)-10-(1,1-dimethyl-1-propyl)-3,7,11-trimethyl-2,4,6,8,10-dodecapentaenoamide,
N-3-hydroxyhexyl (E)-10-(1,1-dimethyl-1-propyl)-3,7,11-trimethyl-2,4,6,8,10-dodecapentaenoamide,
N,N-dimethyl (E)-10 (1,1-dimethyl-1-propyl)-3,7,11-trimethyl-2,4,6,8,10-dodecapentaenoamide,
N-ethyl-N-methyl (E)-10-(1,1-dimethyl-1-propyl)-3,7,11-trimethyl-2,4,6,8,10-dodecapentaenoamide,
N-methyl-N-heptyl (E)-10-(1,1-dimethyl-1-propyl)-3,7,11-trimethyl-2,4,6,8,10-dodecapentaenoamide,
N-phenyl (E)-10-(1,1-dimethyl-1-propyl)-3,7,11-trimethyl-2,4,6,8,10-dodecapentaenoamide,
N-p-hydroxyphenyl (E)-10-(1,1-dimethyl-1-propyl)-3,7,11-trimethyl-2,4,6,8,10-dodecapentaenoamide,
N-p-methoxyphenyl (E)-10-(1,1-dimethyl-1-propyl)-3,7,11-trimethyl-2,4,6,8,10-dodecapentaenoamide,
N-p-butoxyphenyl (E)-10-(1,1-dimethyl-1-propyl)-3,7,11-trimethyl-2,4,6,8,10-dodecapentaenoamide, Examples of carboxamides represented by formula (1)(b) are:
N-methyl (E)-10-(1,1-dimethyl-1-propyl)-3,7,11-trimethyl-2,4,6,8,11-dodecapentaenoamide,
N-isopropyl (E)-10-(1,1-dimethyl-1-propyl)-3,7,11-trimethyl-2,4,6,8,11-dodecapentaenoamide,
N-pentyl (E)-10-(1,1-dimethyl-1-propyl)-3,7,11-trimethyl-2,4,6,8,11-dodecapentaenoamide,
N-octyl (E)-10-(1,1-dimethyl-1-propyl)-3,7,11-trimethyl-2,4,6,8,11-dodecapentaenoamide,
N-2-hydroxyethyl (E)-10-(1,1-dimethyl-1-propyl)-3,7,11-trimethyl-2,4,6,8,11-dodecapentaenoamide,
N-3-hydroxypropyl (E)-10-(1,1-dimethyl-1-propyl)-3,7,11-trimethyl-2,4,6,8,11-dodecapentaenoamide,
N-3-hydroxyhexyl (E)-10-(1,1-dimethyl-1-propyl)-3,7,11-trimethyl-2,4,6,8,11-dodecapentaenoamide,
N,N-dimethyl (E)-10-(1,1-dimethyl-1-propyl)-3,7,11-trimethyl-2,4,6,8,11-dodecapentaenoamide,
N-ethyl-N-methyl (E)-10-(1,1-dimethyl-1-propyl)-3,7,11-trimethyl-2,4,6,8,11-dodecapentaenoamide,
N-methyl-N-heptyl (E)-10-(1,1-dimethyl-1-propyl)-3,7,11-trimethyl-2,4,6,8,11-dodecapentaenoamide,
N-phenyl (E)-10-(1,1-dimethyl-1-propyl)-3,7,11-trimethyl-2,4,6,8,11-dodecapentaenoamide,
N-p-hydroxyphenyl (E)-10-(1,1-dimethyl-1-propyl)-3,7,11-trimethyl-2,4,6,8,11-dodecapentaenoamide,
N-p-methoxyphenyl (E)-10-(1,1-dimethyl-1-propyl)-3,7,11-trimethyl-2,4,6,8,11-dodecapentaenoamide,
N-p-butoxyphenyl (E)-10-(1,1-dimethyl-1-propyl)-3,7,11-trimethyl-2,4,6,8,11-dodecapentaenoamide.

The retinoids and corresponding 2Z isomers of formula (1)(a), and (1)(b) may be made in a stereospecific manner by the following scheme:

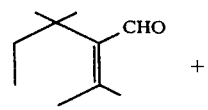

(I)

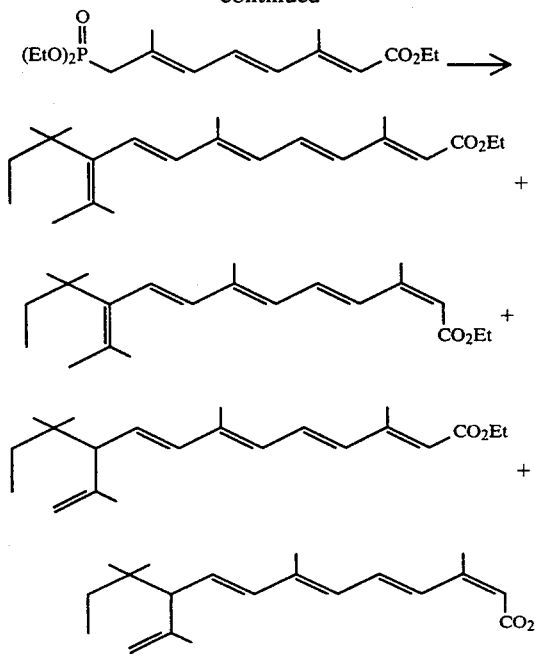

Et=ethyl.

Other esters may be made by substituting various alkoxys for the ethoxy of the triene phosphonate. The amides may likewise be made by starting with the amide. The acids are generally prepared by alkaline hydrolysis of the ethyl esters (Et=ethyl) e.g.:

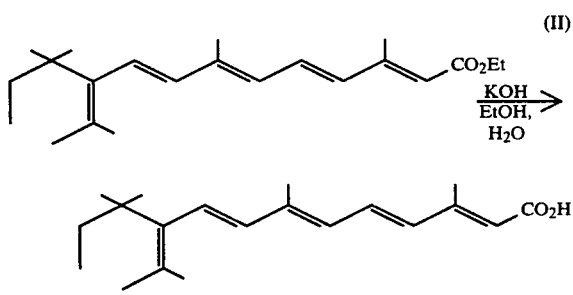

The amides may also then be made from the acids by conversion to acid chlorides or activated ester followed by reaction with an appropriate amine.

The above synthesis (I) was used to make ethyl (E)-10-(1,1-dimethyl-1-propyl)-3,7,11-trimethyl-2,4,6,8,10-dodecapentaenoate and its 2Z isomer as follows. The abbreviations used in the following description are: Ac=H₃CC(O)—; Et=ethyl; Bu=butyl; Me=methyl; NMR=nuclear magnetic resonance; TLC=thin layer chromatography; IR=infrared; THF=tetrahydrofuran; DIBAL=diisobutylaluminum hydride; LC=high-performance liquid chromatography; DME=dimethoxyethane; UV=ultraviolet; and HMPA=hexamethylphosphoramide.

PREPARATION OF ETHYL (E)-10-(1,1-DIMETHYL-1-PROPYL)-3,7,11-TRIMETHYL-2,4,6,8,10-DODECAPENTAENOATE AND ITS 2Z ISOMER 3,3-Dimethyl-2-pentanol. To 36 g (1.5 g-at) of powdered Mg (20–100 mesh) under argon was added 20 mL of dry THF. A 5-mL portion of 2-chloro-2-methylbutane and 0.5 mL of MeI were added. The reaction started immediately. More THF (150 mL) was added, followed by the dropwise addition of the remainder of the 106.6 g (1 mol total) of 2-chloro-2-methylbutane in 60 mL of THF. The addition was completed in 1.5 h. The mixture was heated under reflux for a further 45 min and then cooled in a $-10°$ C. bath. A solution of 68 mL (1.22 mol) of acetaldehyde in 50 mL of THF was added dropwise over a period of 1 h, maintaining the reaction temperature at $-5°$ C. to $0°$ C. The reaction mixture was warmed to room temperature, and the greyish solution was decanted onto 1 L of ice-water containing 60 mL of concentrated $H_2SO_4$. The product was extracted into 300 mL of $Et_2O$. The ethereal layer was washed repeatedly with 500-mL portions of cold water to remove most of the THF, and was then dried ($Na_2SO_4$) and distilled. The colorless liquid distilling at 145°–147° C. was collected (52 g). The fraction distilling between 95° C. and 145° C. was redistilled to give another 6.5 g of product (50% total yield): IR (film) 3350 (OH), 2950, 1470, 1370, 1090, 1040, 1010, 930, 900 cm$^{-1}$; $^1$H NMR (CDCl$_3$) $\delta$0.82, 0.85 [2 s, 6, C(CH$_3$)$_2$], 0.84 (t, J=7 Hz, 3, CH$_2$CH$_3$), 1.12 (d, J=7 Hz, 3, CHCH$_3$), 1.24 (q, J=7 Hz, 2, CH$_2$CH$_3$), 1.94 (broad s, 1, OH), 3.61 (q, J=7 Hz, 1, CHOH).

3,3-Dimethyl-2-pentanone. To a mixture of 270 mL (3.34 mol) of pyridine and 1 L of CH$_2$Cl$_2$ cooled to 0° C. was added 150 g (1.5 mol) of CrO$_3$ in small portions over a period of 1 h. The mixture was mechanically stirred at 0° C. for 15 min. 3,3-Dimethyl-2-pentanol (38 g, 0.33 mol) in 50 mL of CH$_2$Cl$_2$ was added over 30 min while the reaction temperature was maintained at $-5°$ to 0° C. The reaction mixture was then stirred at room temperature for 2 h. Next, it was filtered through a 4.5×15-cm column of Florisil (2 L of CH$_2$Cl$_2$ wash). The filtrate was distilled to remove most of the CH$_2$Cl$_2$. The remaining mixture (about 500 mL) was washed repeatedly with dilute H$_2$SO$_4$ to remove the pyridine, dried (Na$_2$SO$_4$), and fractionated to give 30.4 g (81% yield) of 3,3-dimethyl-2-pentanone as a colorless oil, bp 135° C. IR(film) 2950, 1715 (C=O), 1460, 1350, 1240, 1140, 1100, 1010, 900 cm$^{-1}$; $^1$H NMR (CDCl$_3$) $\delta$0.7–0.95 (m, 5, CH$_2$CH$_3$), $\delta$1.07 [s, 6, C(CH$_3$)$_2$], 2.07 (s, 3, COCH$_3$).

3,4,4-Trimethyl-2-hexenenitrile. NaH (7.1 g, 59.3% dispersion in mineral oil, 0.175 mol) was washed with pentane (3×20 mL) and suspended in 200 mL of dry DME. A solution of 31.07 g (0.175 mol) of diethyl cyanomethylphosphonate in 20 mL of DME was added over 15 min while the reaction mixture was cooled in an ice bath. When no more H$_2$ was evolved, the cooling bath was removed and a solution of 20 g (0.175 mol) of 3,3-dimethyl-2-pentanone in 40 mL of DME was added. The mixture was stirred at room temperature for 60 h. It was diluted with 500 mL of H$_2$O and extracted with 200 mL of Et$_2$O. The ethereal layer was dried (Na$_2$SO$_4$) and concentrated to give 24 g of a colorless oil, which was distilled (bp 116° C., 35 mm) to give 20.8 g (87% yield) of pure 3,4,4-trimethyl-2-hexenenitrile: IR (film) 2950, 2230 (C≡N), 1620 (C=C), 1470, 1380, 1130, 1010, 820 cm$^{-1}$; $^1$H NMR (CDCl$_3$) $\delta$0.77 (t, J=7 Hz, 3, CH$_2$CH$_3$), 1.07 [s, 6, C(CH$_3$)$_2$], 1.50 (q, J=7 Hz, 2, CH$_2$CH$_3$), 2.05 (s, 3, CH$_3$C=C), 5.13 (s, 1, CHCN); MS calcd for C$_9$H$_{15}$N 137.1204, found 137.1205.

2,2-Dimethyl-3-(1,1-dimethyl-1-propyl)-3-butenenitrile. To a solution of 70 mL (0.5 mol) of diisopropylamine in 300 mL of dry THF at $-20°$ C. was added 347.5 mL (0.5 mol) of a 1.44M solution of n-BuLi in hexane over 20 min. The mixture was stirred at −20° C. for 5 min and at 0° C. for 15 min. It was cooled to −78° C., and 270 mL (1.55 mol) of dry HMPA was added over a period of 30 min. The mixture was stirred at −78° C. for 30 min. Then 17.13 g (0.13 mol) of 3,4,4-trimethyl-2-hexenenitrile (20 mL THF rinse) was added slowly so that the reaction temperature remained below −70° C. The solution became bright yellow. Stirring was continued for another 15 min at −78° C. The reaction was then quenched by addition of 50 mL (0.8 mol) of MeI dropwise over a period of 30 min. The reaction mixture was warmed to room temperature, diluted with 1 L of ice-water, and extracted with 500 mL of Et$_2$O. The ethereal layer was washed with saturated NH$_4$Cl (2×300 mL), dried (Na$_2$SO$_4$), and concentrated to give 24 g of a light yellow oil, which was passed over 400 g of silica gel (10% Et$_2$O/hexane) to afford 19.8 g of 2,2-dimethyl-3-(1,1-dimethyl-1-propyl)-3-butenenitrile as a colorless oil. Distillation (bp 99° C., 17 mm) gave 18.7 g (97% yield) of the pure butenenitrile: IR (film) 2950, 2250 (C≡N), 1620 (C═C), 1480, 1390, 1200, 1120, 1020, 900 cm$^{-1}$; $^1$H NMR (CDCl$_3$) δ0.80 (t, J=7 Hz, 3, CH$_2$CH$_3$), 1.23 [s, 6, C(CH$_3$)$_2$], 1.60 [s, 6, C(CH$_3$)$_2$CN], 1.73 (q, J=7 Hz, 2, CH$_2$CH$_3$), 5.07 (s, 2, C═CH$_2$); MS calcd for C$_{11}$H$_{19}$N 165.1517, found 165.1507.

2-(1,1-Dimethyl-1-propyl)-3-methyl-2-buten-1-ol. A mixture of 15 g (0.091 mol) of 2,2-dimethyl-3-(1,1-dimethyl-1-propyl)-3-butenenitrile, 31.5 g (0.183 mol) of m-chloroperbenzoic acid, and 30 g of Na$_2$HPO$_4$ in 375 mL of CH$_2$Cl$_2$ was stirred at room temperature for 60 h. A 10% solution of Na$_2$SO$_3$ (200 mL) was added, and the product was extracted with 300 mL of Et$_2$O. The Et$_2$O layer was dried (Na$_2$SO$_4$) and concentrated to give 22 g of a light yellow oil, which was filtered through 400 g of silica gel (12.5% Et$_2$O/hexane). The pure epoxynitrile (15.1 g, 92% yield) was obtained as a colorless oil: IR (film) 2950, 2250, 1490, 1400, 1210, 1100, 950, 915, 850 cm$^{-1}$; $^1$H NMR (CDCl$_3$) δ0.93 (t, J=7 Hz, 3, CH$_2$CH$_3$), 1.03, 1.15 [2 s, 6, C$_2$H$_5$C(CH$_3$)$_2$], 1.40, 1.50 [2 s, 6, C(CH$_3$)$_2$CN], 1.68 (q, J=7 Hz, 2, CH$_2$CH$_3$), 2.62, 2.82 (2 d, J=3.5 Hz, 2, CH$_2$O); MS calcd for C$_9$H$_{14}$NO (M—C$_2$H$_5$) 152.1075, found 152.1063.

To a solution of 16 g (0.7 mol) of Na in 1 L of liquid NH$_3$ at −78° C. was added 13 g (0.072 mol) of the above epoxynitrile in 10 mL of dry Et$_2$O. The mixture was stirred at −78° C. for 1.5 h before a saturated NH$_4$Cl solution was added to discharge the blue color. The NH$_3$ was evaporated off, and the residue was dissolved in 250 mL of H$_2$O. Extraction with Et$_2$O and concentration gave 9.5 g of a viscous oil, which was fractionated on 250 g of silica gel (25% Et$_2$O/hexane) to give 5 g of the unreacted epoxynitrile and 3.3 g (48% yield based on the amount of epoxynitrile consumed) of the 2-(1,1-dimethyl-1-propyl)-3-methyl-2-buten-1-ol as a colorless oil: IR (film) 3350 (OH), 2950, 1640, 1500, 1370, 1090, 1000 cm$^{-1}$; $^1$H NMR (CDCl$_3$) δ0.78 (t, J=7.5 Hz, 3, CH$_2$CH$_3$), 1.22 [s, 6, C(CH$_3$)$_2$] 1.55 (q, J=7.5 Hz, 2, CH$_2$CH$_3$), 1.87 [s, 6, C═C(CH$_3$)$_2$], 4.13 (s, 2, CH$_2$OH).

2-(1,1-Dimethyl-1-propyl)-3-methyl-2-butenal. A solution of 2.73 mL (30 mmol) of (COCl)$_2$ in 70 mL of CH$_2$Cl$_2$ was cooled to −60° C. Anhydrous Me$_2$SO (4.69 mL, 60 mmol) in 5 mL of CH$_2$Cl$_2$ was added. The mixture was stirred at −60° C. for 5 min before the 2-(1,1-dimethyl-1-propyl)-3-methyl-2-buten-1-ol (2.3 g, 11.7 mmol) in 5 ml of CH$_2$Cl$_2$ was added. This mixture was stirred for 5 min at −60° C. Et$_3$N (20 mL) was added. After another 5 min at −60° C., the mixture was allowed to warm to room temperature, diluted with 100 mL of H$_2$O and extracted with 100 mL of Et$_2$O. The ethereal extract was washed with 100 mL of brine, dried (Na$_2$SO$_4$), and concentrated to give a yellow oil, which was eluted through 150 g of silica gel (10% EtOAc/hexane) to give 1.64 g (72% yield) of the labile aldehyde, 2-(1,1-dimethyl-1-propyl)-3-methyl-2-butenal: IR (film) 3000, 2720, (CHO), 1700 (C═O), 1630 (C═C), 1470, 1375, 1260, 1010, 900, 700 cm$^{-1}$; $^1$H NMR (CCl$_4$) δ0.83 (t, J=Hz, 3, CH$_2$CH$_3$), 1.22 [s, 6, C(CH$_3$)$_2$], 1.67 (q, J=7 Hz, 2, CH$_2$CH$_3$), 1.87, 1.97 [2 s, 6, C═C(CH$_3$)$_2$], 9.57 (s, 1, CHO).

Ethyl (E)-10-(1,1-Dimethyl-b 1-propyl)-3,7,11-trimethyl-2,4,6,8,10-dodecapentaenoate. To a solution of 4.27 g (12.94 mmol) of the triene phosphonate, diethyl (E)-7-carbethoxy-2,6-dimethyl-2,4,6-heptatrienylphosphonate in 60 mL of THF cooled to −78° C. was added 8.5 mL (12.92 mmol) of a 1.52M solution of n-BuLi in hexane over a 5-min period. A bright red solution of the anion formed. It was warmed to room temperature over a 30-min period. 2-(1,1-Dimethyl-1-propyl)-3-methyl-2-butenal (1.64 g, 10.65 mmol) in 2 mL of THF was added. The mixture was stirred at room temperature for 16 h. Water (100 mL) was added, and the product was extracted with 10% EtOAc/hexane (2×50 mL). The organic layer was dried (Na$_2$SO$_4$) and concentrated to give a light brown oil, which was eluted through 100 g of silica gel (5% EtOAc/hexane) to give 1.5 g of a yellow oil (43% yield). Analytical LC (Radialpak B, 1% Et$_2$O/hexane, 2 mL/min, 260 nm) revealed 5 peaks:

(1) ethyl (2Z,4E,6E,8E)-10-(1,1-dimethyl-1-propyl)-3,7,11-trimethyl-2,4,6,8,10-dodecapentaenoate t$_R$ 7.2 min (9%); (2) t$_R$ 8.5 min (24%); (3) ethyl (2E,4E,6Z,8E)-10-(1,1-dimethyl-1-propyl)-3,7,11-trimethyl-2,4,6,8,11-dodecapentaenoate t$_R$ 9.2 min (16%); (4) ethyl (E)-10-(1,1-dimethyl-1-propyl)-3,7,11-trimethyl-2,4,6,8,10-dodecapentaenoate t$_R$ 10.2 min (19%); and (5) ethyl (E)-10-(1,1-dimethyl-1-propyl)-3,7,11-trimethyl-2,4,6,8,11-dodecapentaenoate t$_R$ 11.3 min (32%). Repeated passes using preparative LC (0.4% or 1% Et$_2$O/hexane) gave 300 mg (9%) of fifth isomer, 120 mg (3.4%) of first isomer, 130 mg (3.7%) of fourth isomer, and 40 mg (1.1%) of a sample of third isomer, containing some of the first and fourth isomers.

Ethyl (2Z,4E,6E,8E)-10-(1,1-dimethyl-1-propyl)-3,7,11-trimethyl-2,4,6,8,10-dodecapentaenoate: LC (Radialpak B, 1% Et$_2$O/hexane, 2 mL/min, 260 nm) t$_R$ 7.0 (97%), 7.8 min (3%); LC (Radialpak A, reverse phase, 5% H$_2$O/MeOH, 2 mL/min, 260 nm) t$_R$ 3.4 (2%), 4.8 (1%), 6.4 min (97%); IR (CCl$_4$) 2950, 1710, 1620, 1600, 1450, 1380, 1230, 1150, 1050, 970, 870, 850 cm$^{-1}$; $^1$H NMR (CDCl$_3$) δ0.82 (t, J=7.5 Hz, 3, CH$_2$CH$_3$), 1.10 (s, 6 16$_R$, 17$_R$ CH$_3$), 1.28 (t, J=7 Hz, 3, CO$_2$CH$_2$CH$_3$), 1.55 (q, J=7.5 Hz, 2, CH$_2$CH$_3$), 1.72, 1.84 [2 s, 6, C═C(CH$_3$)$_2$], 1.98 (s, 3, 19$_R$ CH$_3$) 2.06 (s, 3, 20$_R$ CH$_3$), 4.16 (q, J=7.5 Hz, 2, CO$_2$CH$_2$CH$_3$), 5.63 (s, 1, 14$_R$ C═CH), 5.90 (d, J=16 Hz, 1, 8$_R$ HC═CH), 6.20 (d, J=16 Hz, 1, 7$_R$ HC═CH), 6.21 (d, J=11 Hz, 1, 10$_R$ C═CH), 6.97 (dd, J=11, 16 Hz, 1, 11$_R$ HC═CH), 7.76 (d, J=16 Hz, 1, 12$_R$ HC═CH); $^{13}$C NMR (CDCl$_3$) 9.3, 14.4 [C═C(CH$_3$)$_2$], 13.0 (19$_R$), 20.9 (20$_R$), 22.5 (3$_R$), 25.8 (2$_R$), 29.1 (16$_R$, 17$_R$), 35.1 (1$_R$), 39.4 (ester CH$_3$), 59.6 (ester CH$_2$), 116.6 (14$_R$), 128.5 (7$_R$), 129.2 (5$_R$), 129.8 (12$_R$), 132.0, 133.6 (10$_R$, 11$_R$), 136.3, 138.6 (6$_R$, 8$_R$), 139.6 (9$_R$), 150.9(13$_R$), 166.3 ppm (C═O); UV (EtOH) $\lambda_{max}$ 244 nm ($\epsilon 9.2 \times 10^3$), 355 nm ($\epsilon 3.6 \times 10^4$); MS calcd for $C_{22}H_{34}O_2$ 330.2559, found 330.2551.

Ethyl (2E,4E,6Z,8E)-10-(1,1-dimethyl-1-propyl)-3,7,11-trimethyl-2,4,6,8,11-dodecapentaenoate: LC (Radialpak B, 1% Et$_2$O/hexane, 2 mL/min, 260 nm) $t_R$ 7.8 (2.6%), 8.6 (73.4%), 9.3 min (24%); LC (Radialpak A, reverse phase, 5% H$_2$O/MeOH, 2 mL/min, 260 nm) $t_R$ 4.0 (2%), 5.8 (24%), 6.6 (70%), 7.5 min (4%); $^1$H NMR (CDCl$_3$) $\delta$0.84 (t, J=7 Hz, 3, CH$_2$CH$_3$), 0.88, 0.89 [2 s, 6, C(CH$_3$)$_2$], 1.28 (q, J=7 Hz, 2, CH$_2$CH$_3$), 1.29 (t, J=7 Hz, 3, CO$_2$CH$_2$CH$_3$), 1.79 (s, 3, H$_2$C=CCH$_3$), 1.96 (s, 3, 19$_R$ CH$_3$), 2.35 (s, 3, 20$_R$ CH$_3$) 2.70 (d, J=8 Hz, 1, 6$_R$ CH), 4.17 (q, J=7 Hz, 2, CO$_2$CH$_2$CH$_3$), 4.76, 4.87 (2 s, 2, C=CH$_2$), 5.76 (s, 1, 14$_R$ C=CH), 6.01 (d, J=11 Hz, 1, 10$_R$ C=CH). 6.02 (dd, J=8, 16 Hz, 1, 7$_R$ HC=CH), 6.21 (d, J=16 Hz, 1, 12$_R$ HC=CH), 6.59 (d, J=16 Hz, 1, 8$_R$ HC=CH), 7.07 (dd, J=11, 16 Hz, 1, 11$_R$ HC=CH); $^{13}$C NMR (CDCl$_3$) 8.4, 14.4, 23.9 (2$_R$, 3$_R$, 4$_R$), 14.0 (20$_R$), 21.3 (9$_R$), 24.5, 24.7 (16$_R$, 17$_R$), 33.3 (1$_R$), 36.7 (ester CH$_3$), 59.6, 60.0 (6$_R$, ester CH$_2$), 113.4, 118.6 (14$_R$), 127.3, 127.7, 129.7, 133.7, 134.5 (12$_R$), 138.1, 146.4, 152.7, (13$_R$), 167.1 ppm (C=O); UV (EtOH) $\lambda_{max}$ 248 nm ($\epsilon 6.7 \times 10^3$), 341 nm ($4.1 \times 10^4$); MS calcd for $C_{22}H_{34}O_2$ 330.2559, found 330.2551.

Ethyl (E)-10-(1,1-dimethyl-1-propyl)-3,7,11-trimethyl-2,4,6,8,10-dodecapentaenoate: LC (Radialpak B, 1% Et$_2$O/hexane, 3 mL/min, 260 nm) $t_R$ 6.0 (2%), 6.5 (97%), 7.4 min (1%); LC (Radialpak A, reverse phase, 5% H$_2$O/MeOH, 2 mL/min, 260 nm) $t_R$ 4.0 (1%), 5.6 (1%), 6.8 (1%), 7.6 min (97%); IR (CCl$_4$) 2950, 1720, 1620, 1600, 1450, 1390, 1370, 1350, 1240, 1150, 1050, 970, 895, 885 cm$^{-1}$; $^1$H NMR (CDCl$_3$) $\delta$0.82 (t, J=7.5 Hz, 3, CH$_2$CH$_3$), 1.10 (s, 6, 16$_R$, 17$_R$ CH$_3$), 1.29 (t, J=7 Hz, 3, CO$_2$CH$_2$CH$_3$), 1.56 (q, J=7.5 Hz, 2, CH$_2$CH$_3$), 1.72, 1.84 [2 s, 6 C=C(CH$_3$)$_2$], 1.98 (s, 3, 19$_R$ CH$_3$), 2.35 (s, 3, 20$_R$ CH$_3$), 4.16 (q, J=Hz, 2, CO$_2$CH$_2$CH$_3$), 5.77 (s, 1, 14$_R$ C=CH), 5.89 (d, J=16 Hz, 1, 8$_R$ HC=CH), 6.10 (d, J=11.5 Hz, 1, 10$_R$ C=CH), 6.20 (d, J=16 Hz, 1, 7$_R$ HC=CH), 6.27 (d, J=16 Hz, 1, 12$_R$ HC=CH), 6.98 (dd, J=11.5, 16 Hz, 1, 11$_R$ HC=CH); $^{13}$C NMR (CDCl$_3$) 9.3, 13.0 (19$_R$), 13.9 (20$_R$), 14.4 [C=C(CH$_3$)$_2$], 22.5 (3$_R$), 25.8 (2$_R$), 29.1 (16$_R$, 17$_R$), 35.1 (1$_R$), 39.4 (ester CH$_3$), 59.6 (ester CH$_2$), 118.5 (14$_R$), 128.4 (7$_R$), 129.0 (5$_R$), 130.8, 133.7 (10$_R$, 11$_R$), 135.0 (12$_R$), 136.1, 138.6 (6$_R$, 8$_R$), 139.4 (9$_R$), 152.6 (13$_R$), 167.1 ppm (C=O); UV (EtOH) $\lambda_{max}$ 245 nm ($\epsilon 4.4 \times 10^3$), 351 nm ($\epsilon 3.9 \times 10^4$); MS calcd for $C_{22}H_{34}O_2$ 330.2551, found 330.2559.

Ethyl (E)-10-(1,1-dimethyl-1-propyl)-3,7,11-trimethyl-2,4,6,8,11-dodecapentaenoate: LC (Radialpak B, 1% Et$_2$O/hexane, 2 mL/min, 260 nm) $t_R$ 13.4 (2%), 15.1 min (98%); LC (Radialpak A, reverse phase, 5% H$_2$O/MeOH, 2 mL/min, 260 nm) $t_R$ 3.4 (2%), 6.5 (97%), 7.6 min (1%); IR (film) 2950, 1710, 1620, 1600, 1450, 1390, 1370, 1350, 1230, 1150, 1050, 970, 890 cm$^{-1}$; $^1$H NMR (CDCl$_3$) $\delta$0.82 (t, J=7.5 Hz, 3, CH$_2$CH$_3$), 0.86, 0.87 (2 s, 6, 16$_R$, 17$_R$ CH$_3$), 1.27 (q, J=7.5 Hz, 2, CH$_2$CH$_3$), 1.28 (t, J=7 Hz, 3, CO$_2$CH$_2$CH$_3$), 1.78 (s, 3, H$_2$C=CCH$_3$), 1.96 (s, 3, 19$_R$ CH$_3$), 2.34 (s, 3, 20$_R$ CH$_3$), 2.54 (d, J=8 Hz, 1, 6$_R$ H), 4.17 (q, J=7 Hz, 2, CO$_2$CH$_2$CH$_3$), 4.73, 4.85 (2 s, 2, C=CH$_2$), 5.76 (s, 1, 14$_R$ C=CH), 5.97 (dd, J=8, 16 Hz, 1, 7$_R$ HC=CH), 6.10 (d, J=16 Hz, 1, 8$_R$ HC=CH), 6.10 (d, J=11 Hz, 1, 10$_R$C=CH), 6.25 (d, J=16 Hz, 1, 12$_R$ HC=CH), 6.95 (dd, J=11, 16 Hz, 1, 11$_R$ HC=CH); $^{13}$C NMR (CDCl$_3$) 8.3, 14.4, 23.6 (2$_R$, 3$_R$, 4$_R$), 13.2 (9$_R$), 13.8 (20$_R$), 24.4, 24.7 (16$_R$, 17$_R$), 33.3 (1$_R$), 36.6 (ester CH$_3$), 59.6, 59.7 (ester CH$_2$, 6$_R$), 113.3, 118.7 (14$_R$), 129.3, 130.7, 131.8, 135.2 (12$_R$), 139.0, 146.5, 152.5 (13$_R$), 167.1 ppm (C=O); UV (EtOH) $\lambda_{max}$ 244 nm ($\epsilon 5.2 \times 10^3$), 345 nm ($\epsilon 4.8 \times 10^4$); MS calcd for $C_{22}H_{34}O_2$ 330.2551, found 330.2559.

The retinoids of formula (1) may be used topically or systemically as chemopreventive agents and in the treatment, amelioration, or prevention of skin, rheumatic or other disorders for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, keratosis, atopic dermatitis, nonspecific dermatitis and the like. When used for such treatments they will usually be formulated with a pharmaceutical liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be more than topical doses and doses for treating skin disorders will typically be less than doses administered for cancer chemoprevention. The dose for treating skin disorders will be on the order of, but normally less than, the dose of retinoic acid prescribed for the disorder.

The usefulness of the invention compounds was demonstrated by testing the compounds of the Examples in the ornithine decarboxylase (ODC) assay, Verma, A. K. and Boutwell, R. K., *Cancer Res* (1977) 37:2196–2201, and the tracheal organ culture assay, Newton, D. L.; Henderson, W. R.; and Sporn, M. B., *Cancer Res* (1980) 40:3413–3425. The ODC assay measures a compound's ability to prevent the induction of ODC by tumor promoters. The tracheal organ culture assay measures a compound's ability to reverse keratinization.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 μg, 17 nmol) in 0.2 mL of acetone is applied topically to the back of each mouse. The test compound, at one of three dose levels (1.7, 17 and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15-20 seconds in 50 mM sodium phosphate and 0.1 mM ethylenediaminetetraacetic acid (EDTA), at a volume of 1 mL/skin.

The supernatant fraction remaining after centrifugation of the homogenate at 10,000×g for 30 seconds at 0° C. is used for the enzyme assay. Enzyme activity is determined using the microassay for ODC as described by Verma and Boutwell to measure the release of $^{14}CO_2$ from $DL-[1-^{14}C]$-ornithine (58 mCi/mmol) after incubation with the 10,000×g supernatant. The incubations are carried out by decanting, with a Pasteur pipette, 100 μL of the supernatant containing 100 to 120 μg of protein into two or three 15-mL Corex tubes in a shaking water bath at 37° C. The assay mixture in the tubes consists of 50 μL of 100 mM sodium phosphate buffer (pH 7.2), 10 μL of 4 mM pyridoxal phosphate, 40 μL of 25 mM dithiothreitol, and 1 μL of 0.1M EDTA. The center wells in the tubes are filled with 200 μL of a 2:1 solution (v/v) of ethanolamine:2-methoxyethanol. The reaction is started by adding 50 μL of substrate (0.5 μCi of $DL-[1-^{14}C]$-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 μg/ml; hydrocortisone hemisuccinate, 0.1 μg/ml; glutamine, 2 mM; penicillin, 100 units/ml; and streptomycin, 100 μg/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

|  | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
|  | Conc. (M) | Active/Total Cultures (%) | Dose (nmol) | Inhibition of Control |
| Controls |  |  |  |  |
| Retinoic Acid | $10^{-8}$ | 236/236 (100) | 1.7 | 87–91 |
|  | $10^{-9}$ | 419/474 (88) |  |  |
|  | $10^{-10}$ | 134/256 (52) |  |  |
| Ethyl Retinoate | $10^{-8}$ | 53/55 (96) |  |  |
|  | $10^{-9}$ | 20/29 (69) |  |  |
|  | $10^{-10}$ | 0/12 (0) |  |  |
| Compounds |  |  |  |  |
| Ethyl (E)—10-(1,1-Dimethyl-1-propyl)-3,7,11-trimethyl-2,4,5,6,8,10-dodecapentaenoate | $10^{-8}$ | 12/12 (100) | 17 | 81 |
|  | $10^{-9}$ | 10/12 (83) | 1.7 | 40 |
|  | $10^{-10}$ | 3/11 (27) |  |  |
| Ethyl (E)—10-(1,1-Dimethyl-1-propyl)-3,7,11-trimethyl-2,4,6,8,11-dodecapentaenoate | $10^{-8}$ | 10/11 (91) | 17 | 54 |
|  | $10^{-9}$ | 10/13 (77) | 1.7 | 0 |
|  | $10^{-10}$ | 4/11 (36) |  |  |
| Ethyl (2Z,4E,6E,8E)—10-(1,1-Dimethyl-1-propyl)-3,7,11-trimethyl-2,4,6,8,10- | $10^{-8}$ | 11/11 (100) | 17 | 20 |
|  | $10^{-9}$ | 7/10 (70) | 1.7 | 14 |
|  | $10^{-10}$ | 3/10 (30) |  |  |

| | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
| | Conc. (M) | Active/Total Cultures (%) | Dose (nmol) | Inhibition of Control |
| dodecapentaenoate | | | | |

These results indicate that the open chain retinoids of the invention possess biological activity that makes them useful as chemopreventive agents and therapeutic agents for treating nonmalignant skin disorder.

Modifications of the above described modes for carrying out the invention that are obvious to those of skill in the fields of organic chemistry, pharmaceuticals, and/or medicine are intended to be within the scope of the following claims.

What is claimed is:

1. A compound of the formula:

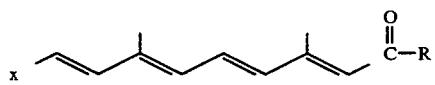

and 2Z isomers thereof where X is

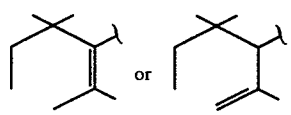

and R is hydroxy, alkoxy with 0 or 1 hydroxy substituent, aroxy or $NR^1R^2$ where $R^1$ is hydrogen, alkyl with 0 or 1 hydroxy substituent, aryl and $R^2$ is alkyl with 0 or 1 hydroxy or aryl.

2. A compound of claim 1 wherein the alkoxy group represented by R contains 1 to about 10 carbon atoms with 0 or 1 hydroxy substituent, the aroxy group represented by R contains 6 to about 15 carbon atoms, the alkyl groups represented by $R^1$ and $R^2$ each contain 1 to about 8 carbon atoms with 0 or 1 hydroxy substituent and the aryl groups represented by $R^1$ and $R^2$ each contain 6 to about 15 carbon atoms.

3. The compound of claim 1 where the alkoxy group represented by R contains 1 to 4 carbon atoms and have 0 or 1 hydroxy substituent, the aroxy group represented by R is phenoxy, monohydroxy phenoxy, or monoalkoxyphenoxy where the alkoxy group contains 1 to 4 carbon atoms, the alkyl groups represented by $R^1$ and $R^2$ each contain 1 to 4 carbon atoms and have 0 or 1 hydroxy substituent, and the aryl groups represented by $R^1$ and $R^2$ are phenyl, 4-hydroxyphenyl, or 4-methoxyphenyl.

4. The compound of claim 1 where R is ethoxy or hydroxy.

5. The compound:

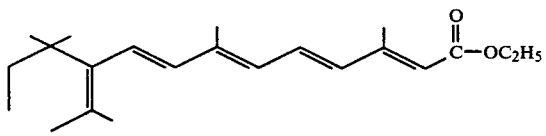

and its 2Z isomer.

6. The compound:

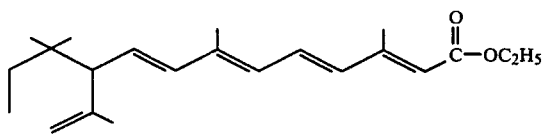

and its 2Z isomer.

7. A pharmaceutical composition comprising a pharmaceutically effective amount of the compound of claim 1 combined with a pharmaceutically acceptable carrier.

8. A pharmaceutical composition comprising a pharmaceutically effective amount of the compound of claim 2 combined with a pharmaceutically acceptable carrier.

9. A pharmaceutical composition comprising a pharmaceutically effective amount of the compound of claim 3 combined with a pharmaceutically acceptable carrier.

10. A pharmaceutical composition comprising a pharmaceutically effective amount of the compound of claim 4 combined with a pharmaceutically acceptable carrier.

11. A pharmaceutical composition comprising a pharmaceutically effective amount of the compound of claim 5 combined with a pharmaceutically acceptable carrier.

12. A pharmaceutical composition comprising a pharmaceutically effective amount of the compound of claim 6 combined with a pharmaceutically acceptable carrier.

* * * * *